(12) United States Patent
Colonno et al.

(10) Patent No.: US 6,627,224 B2
(45) Date of Patent: Sep. 30, 2003

(54) LOW DOSE ENTECAVIR FORMULATION AND USE

(75) Inventors: Richard J. Colonno, Farmington, CT (US); Omar L. Sprockel, Bridgewater, NJ (US); Abizer Harianawala, North Brunswick, NJ (US); Divyakant Desai, West Windsor, NJ (US); Michael G. Fakes, Belle Mead, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 09/792,576

(22) Filed: Feb. 23, 2001

(65) Prior Publication Data

US 2001/0033864 A1 Oct. 25, 2001

Related U.S. Application Data

(60) Provisional application No. 60/185,672, filed on Feb. 29, 2000, and provisional application No. 60/221,313, filed on Jul. 28, 2000.

(51) Int. Cl.$^7$ .............. A61K 9/16; A61K 9/20; A61K 9/28; A61K 9/48
(52) U.S. Cl. .......... 424/480; 424/451; 424/464; 424/474; 424/482; 424/489; 424/490; 514/770; 514/772.3; 514/774; 514/777; 514/778; 514/781; 514/782; 514/784
(58) Field of Search .............. 424/464, 465, 424/451, 474, 475, 480, 482, 489, 490

(56) References Cited

U.S. PATENT DOCUMENTS

| | | | | |
|---|---|---|---|---|
| 4,489,026 A | | 12/1984 | Yalkowsky | 264/123 |
| 4,513,008 A | * | 4/1985 | Revici et al. | 514/560 |
| 4,631,284 A | | 12/1986 | Salpekar et al. | 514/227 |
| 5,206,244 A | | 4/1993 | Zahler et al. | 514/262 |
| 5,997,905 A | | 12/1999 | McTeigue et al. | 424/490 |

FOREIGN PATENT DOCUMENTS

| | | |
|---|---|---|
| WO | 97/37638 | 10/1997 |
| WO | 98/09964 | 3/1998 |
| WO | 00/16754 | 3/2000 |
| WO | 00/16755 | 3/2000 |
| WO | 00/16779 | 3/2000 |
| WO | WO 01/30329 | 5/2001 |

OTHER PUBLICATIONS

Innaimo et al., Antimicrobial Agents and Chemotherapy, vol. 41, No. 7, p. 1444–1448, Jul. 1997.
Seifer et al., Antimicrobial Agents and Chemotherapy, vol. 42, No. 12, p. 3200–3208, Dec. 1998.
Genovesi et al., Antimicrobial Agents and Chemotherapy, vol. 42, No. 12, p. 3209–3217, Dec. 1998.
Yamanaka et al., Antimicrobial Agents And Chemotherapy, vol. 43, No. 1, p. 190–193, Jan. 1999.
Torresi et al., Gastroenterology vol. 118, p. S83–S103, Feb. 2000.
Marion et al., Antiviral Research, vol. 41, No. 2, p. A55, Mar. 1999.
Marion et al., 38$^{th}$ Interscience Conference on Antimicrobial Agents and Chemotherapy, p. 329, Sep. 24, 1998.
Grasela et al., 37$^{th}$ Interscience Conference on Antimicrobial Agents and Chemotherapy, p. 219, Sep. 28, 1997.
Goodhart, Journal of Pharmaceutical Sciences, vol. 59, No. 4, p. 540–547, Apr. 1970.
Colonno et al., Hepatology, p. 488A, Oct. 1998.
Bisacchi et al., Bioorganic & Medicinal Chemistry Letters, vol. 7, No. 2, p. 127–132 1997.
Graul et al., Drugs of the Future, vol. 24, No. 11, p. 1173–1177 1999.
DeClercq, International Jour. of Antimicrobial Agents, vol. 12, page 81–95 1999.

* cited by examiner

Primary Examiner—James M. Spear
(74) Attorney, Agent, or Firm—Stephen B. Davis

(57) ABSTRACT

Compositions containing a low dose of entecavir are administered on a daily basis to treat hepatitis B virus infection and/or co-infections. Formulations for the oral administration of a low dose of entecavir are provided. Other pharmaceutically active substances can be included in the entecavir composition or can be separately administered for the treatment of hepatitis B virus infection or for the treatment of co-infected patients.

53 Claims, No Drawings

LOW DOSE ENTECAVIR FORMULATION AND USE

This application claims priority from Ser. No. 60/185,672 filed Feb. 29, 2000 and Ser. No. 60/221,313 filed Jul. 28, 2000.

BACKGROUND OF THE INVENTION

Entecavir, [1S-(1α,3α,4β)]-2-amino-1,9-dihydro-9-[4-hydroxy-3-(hydroxymethyl)-2-methylenecyclopentyl]-6H-purin-6-one

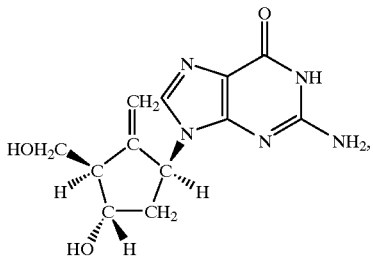

is an antiviral agent currently undergoing clinical evaluation for the treatment of hepatitis B virus infection.

Entecavir and its use in treating hepatitis B are disclosed by Zahler et al. in U.S. Pat. No. 5,206,244. This patent discloses that an effective antiviral dose for oral or parenteral administration will likely be in the range of about 1.0 to 50 mg/kg of body weight and that the desired dose may be administered several times daily at appropriate intervals.

Improved methods for the synthesis of entecavir are disclosed by Bisacchi et al. in WO 98/09964.

BRIEF SUMMARY OF THE INVENTION

This invention is directed to pharmaceutical compositions containing a low dose of entecavir and the use of such low dose composition to safely and effectively treat hepatitis B virus infection.

This invention is also directed to the treatment of hepatitis B virus infection with a low dose of entecavir in combination with other pharmaceutically active agents. Suitable agents for this purpose include other antiviral agents and/or immunomodulators. The entecavir and the other pharmaceutically active agent or agents can be combined into a single dose form or can be administered from separate dose forms at the same time or sequentially according to a prescribed schedule.

This invention is also directed to pharmaceutical compositions for oral administration containing low doses of a pharmaceutically active substance. This result is achieved by adhering particles of the pharmaceutically active substance to the surface of a carrier substrate. The process of depositing the active substance on the carrier substrate is controlled to minimize the agglomeration of the active substance/carrier substrate particles.

DETAILED DESCRIPTION OF THE INVENTION

This invention is directed to pharmaceutical compositions containing a low dose of from about 0.001 mg to about 25 mg of the active antiviral agent entecavir for once daily administration to treat hepatitis B virus infection in an adult human patient. Preferred pharmaceutical compositions contain from about 0.01 mg to about 10 mg of entecavir and most preferred pharmaceutical compositions contain from about 0.01 to about 5 mg of entecavir. Such preferred and most preferred pharmaceutical compositions are also administered once daily to treat hepatitis B virus infection in an adult patient.

The term adult human patient is defined as a patient of about 16 years or more of age and a weight equal to or greater than about 50 kilograms. Pharmaceutical compositions containing entecavir at the lower end of the above ranges are suitable for administration to pediatric patients or adult patients weighing less than about 50 kilograms.

The low dose entecavir pharmaceutical compositions described above for daily administration may also be administered to certain patients less often. For example, patients who have been treated by daily administration of the low dose entecavir pharmaceutical compositions so that their hepatitis B virus infection is now under control may be placed on a maintenance regimen to protect against further infection. Such maintenance therapy may involve the administration of the low dose entecavir composition on a less than daily basis. For example, a single dose administered every three or four days or administered on a weekly basis may be sufficient.

The low dose entecavir pharmaceutical compositions of this invention can be formulated for administration by any suitable means. For example, compositions for oral administration, which are preferred, can be in the form of tablets, capsules, granules or powders or in the form of elixirs, solutions or suspensions. The low dose entecavir pharmaceutical compositions may also be formulated for parenteral, rectal, transdermal or nasal administration according to methods well known in the art. Such formulations can include pharmaceutically acceptable excipients including bulking agents, lubricants, disintegrants, binding agents, etc. as commonly employed in such compositions. Sustained release formulations are also within the scope of this invention.

Surprisingly, it has been found that once daily administration of the low dose entecavir pharmaceutical compositions of this invention are effective in treating hepatitis B virus infection without undesirable side effects that can result from administration of the high dose regimen described in U.S. Pat. No. 5,206,244.

This invention is also directed to the treatment of hepatitis B virus infection with low dose entecavir compositions as described above in combination with one or more other pharmaceutically active agents. Suitable pharmaceutically active agents for this purpose include one or more antiviral agents, for example, didanosine, lamivudine, abacavir, adefovir, adefovir dipivoxil, famciclovir, (2R,4R)-4-(2,6-diamino-9H-purin-9-yl)-2-hydroxymethyl-1,3-dioxolane (DAPD), hepatitis B immunomodulating proteins (EHT 899 from Enzo Biochem), emtricitabine, 1-(2-deoxy-2-fluoro-β-D-arabinofuranosyl) thymine(FMAU), GLQ-223 (Compound A, alpha-trichosanthin), epavudine (L-dT), epcitabine (L-dC), ribavirin, tenofovir (PMPA), 2',3'-dideoxy-2',3'-didehydro-beta-L(−)-5-fluorocytidine [L(−)Fd4C], as well as other fluoro L- and D-nucleosides. Suitable pharmaceutically active agents for this purpose also include one or more immunomodulators, for example, alpha interferon, beta interferon, pegylated interferon, thymosin alpha, and hepatitis B vaccines such as HBV/MF59, Hepagene and Theradigm-HBV.

When the other pharmaceutically active agent or agents are suitable for oral administration, they can be combined with the low dose of entecavir into a single tablet or capsule.

If the other pharmaceutically active agent or agents are not compatable with entecavir for co-administration from a single dosage form, for example, if the mode of administration is different or if the frequency of administration is different, then the other pharmaceutically active agent or agents will be administered separately. The amount of the other agent or agents administered is that conventionally employed in mono therapy or a reduced amount as determined by the treating physician. The separate dose forms can be administered at the same time or sequentially according to a prescribed schedule.

This invention also includes the treatment of co-infected patients with the low dose entecavir compositions described above. A co-infected patient is one infected with other viral or non-viral diseases in addition to hepatitis B. In particular, such treatment is possible for hepatitis B patients co-infected with hepatitis C or HIV. Such co-infected patients are preferably treated with the low dose entecavir compositions as described above in combination with one or more other pharmaceutically active agents as described above. For example, a patient co-infected with hepatitis B and hepatitis C can be treated with the low dose entecavir composition in addition to being treated with a regimen of ribavirin and an interferon.

Another aspect of this invention is the preparation of pharmaceutical compositions, particularly tablets and capsules, containing entecavir in an amount of less than or equal to about 10 mg. Such compositions cannot be prepared with good content uniformity by simply mixing the active substance and the excipients. The traditional methods of granulation are also not suitable for products active at such low doses.

Tablet and capsule formulations containing from about 0.001 mg to about 10 mg of entecavir are prepared according to the following procedures that ensure high potency and good uniformity of the product. The compositions are prepared by first carefully depositing the entecavir on the surface of carrier substrate particles. This step is accomplished by forming a solution of the entecavir in a solvent along with an adhesive substance at temperatures ranging from about 25° C. to about 80° C. and applying the solution as a spray or a stream while the carrier substrate particles are in motion. The conditions are controlled to minimize particle agglomeration. Subsequently, the solvent is removed from the carrier surface leaving the entecavir particles adhered to the surface of the carrier substrate. This prevents the separation of the entecavir from the substrate and minimizes the loss of entecavir during subsequent processing.

Following drying, the entecavir coated carrier substrate particles are mixed with any other ingredients to be included in the composition such as a disintegrant and/or lubricant. The resulting powder is then compressed into tablets or filled into capsules.

The carrier substrate particles are kept in motion during the spraying step by means of mechanical or air stream agitation. In the mechanical agitation procedure, the carrier substrate is placed in a mechanical (high shear) mixer and agitated. A solution containing the entecavir and adhesive substance maintained at a temperature of from about 25° C. to about 80° C. is sprayed onto the carrier substrate particles at a controlled rate and atomizing pressure (0 to 2 bar). To maximize the amount of entecavir deposited on the carrier, the position of the spray assembly is adjusted to make certain that the spray pattern only encompasses the carrier. The rate of deposition and the spray pattern are controlled to minimize particle agglomeration. Once the entecavir containing solution is deposited, the wet entecavir/carrier substrate particles are transferred to a drier, either a tray drier or fluidbed drier is suitable. The solvent is removed at an elevated temperature. When the solvent is water or pH adjusted water, a temperature of from about 50° to about 80° C. is suitable.

In the air stream agitation procedure, the carrier substrate is placed in a bowl with a fine mesh screen at the bottom. The incoming air stream is adjusted so that the substrate particle motion is constant and fluid. The carrier material is equilibrated to a temperature of from about 25° C. to about 80° C. A solution containing the entecavir and adhesive substance maintained at a temperature of from about 25° C. to about 80° C. is sprayed onto the carrier substrate particles at a controlled rate and atomizing pressure as described above. Again, the position of the spray assembly is adjusted to make certain that the spray pattern only encompasses the carrier and the rate of deposition is controlled to minimize particle agglomeration. Once the entecavir solution is deposited, the temperature is elevated to remove the solvent. When the solvent is water or pH adjusted water, a temperature of from about 50° C. to about 80° C. is suitable. In the air stream agitation procedure, both the deposition of the entecavir onto the carrier substrate and the removal of the solvent are carried out in a single unit whereas the mechanical agitation procedure requires a two-unit operation.

The above procedures have the additional advantage of reducing exposure of the manufacturing personnel to entecavir in the atmosphere of the facility.

While the above procedures are described for preparing pharmaceutical compositions containing from about 0.005 mg to about 10 mg of entecavir, they can also be employed to prepare pharmaceutical compositions containing low doses of any soluble pharmaceutically active substance.

Preferred solvents in the above procedures are water and pH adjusted water. The solubility of entecavir in water can be increased by lowering the pH of water by the addition of an acid such as hydrochloric acid or by raising the pH of water by the addition of a base such as ammonium hydroxide.

The adhesive substance is preferably a polymeric material possessing a high degree of tackiness. Suitable materials include povidone, methylcellulose, hydroxymethylcellulose, hydroxypropylmethylcellulose, hydroxypropylcellulose, hydroxyethylcellulose, gelatin, guar gum, and xanthan gum and mixtures thereof with povidone being preferred. The adhesive substance is preferably present in the final composition at from about 0.01% to about 10% by weight of the total composition.

The carrier substrate is a pharmaceutically acceptable substance that can be readily spray coated and yet will not easily agglomerate. Suitable materials include lactose, microcrystalline cellulose, calcium phosphate, dextrin, dextrose, dextrates, mannitol, sorbitol, and sucrose and mixtures thereof with lactose and microcrystalline cellulose and mixtures thereof being preferred. The carrier substrate is preferably present in the final composition at from about 80% to about 95% by weight of the total composition.

A disintegrant is preferably included in the final composition at from about 1% to about 7% by weight of the total composition. Suitable disintegrants include crospovidone, croscarmellose, sodium starch glycolate, pregelatinized starch, and corn starch and mixtures thereof with crospovidone being preferred.

A lubricant is preferably included in the final composition at from about 0.1% to about 5% by weight of the total composition. Suitable lubricants include magnesium stearate, stearic acid, sodium stearyl fumarate, and sodium lauryl sulfate with magnesium stearate being preferred.

The resulting tablet or capsule can be film coated for ease of administration. Suitable materials for use in the film coating are polymeric coating agents, pigments, plasticizers, solubilizing agents, etc. Suitable coating agents include hydroxypropyl methylcellulose, hydroxyethyl cellulose, hydroxypropyl cellulose, hydroxypropyl methylcellulose phthalate, etc. Polyethylene glycol can be included in the film coating composition as a plasticizer. Additional plasticizers such as diethyl citrate and trietyl citrate may also be included in the film coating composition. Suitable solubilizing agents include polyoxyethylene sorbitan fatty acid esters particularly polysorbate 80. Suitable pigments include titanium dioxide and various iron oxides.

The ingredients of the coating compositions are dispersed in a suitable solvent, preferably water. The coating composition can be applied to the tablets or capsules using conventional pan coating or spray coating techniques.

The following examples describe low dose entecavir compositions within the scope of this invention.

EXAMPLE 1

Employing the above procedures a tablet of 0.5 milligram strength entecavir was prepared.

| Ingredient | Amount % weight/weight | Amount per tablet |
|---|---|---|
| Entecavir | 0.5 | 0.50 mg |
| Lactose monohydrate, NF | 60.00 | 60.00 mg |
| Microcrystalline cellulose, NF | 32.50 | 32.50 mg |
| Crospovidone, NF | 4.00 | 4.00 mg |
| Povidone, USP | 2.50 | 2.50 mg |
| Magnesium Stearate, NF | 0.50 | 0.50 mg |
| Purified Water, USP* | q.s. | — |
| Total | 100.00 | 100.00 mg |

*removed by drying

EXAMPLE 2

Employing the above procedures a tablet of 0.1 milligram strength entecavir was prepared.

| Ingredient | Amount % weight/weight | Amount per capsule |
|---|---|---|
| Entecavir | 0.1 | 0.1 mg |
| Lactose monohydrate, NF | 60.00 | 60.00 |
| Microcrystalline cellulose, NF | 35.39 | 35.39 mg |
| Crospovidone, NF | 4.0 | 4.00 mg |
| Povidone, USP | 0.01 | 0.01 mg |
| Magnesium Stearate, NF | 0.5 | 0.5 mg |
| Purified Water, USP* | q.s. | — |
| Total | 100.00 | 100.00 mg |

*removed by drying

EXAMPLE 3

Employing the above procedures a tablet of 0.01 milligram strength entecavir was prepared.

| Ingredient | Amount % weight/weight | Amount per tablet |
|---|---|---|
| Entecavir | 0.01 | 0.01 mg |
| Microcrystalline cellulose, NF | 93.24 | 93.24 mg |
| Crospovidone, NF | 4.00 | 4.00 mg |
| Povidone, USP | 2.50 | 2.50 mg |
| Magnesium Stearate, NF | 0.25 | 0.25 mg |
| Purified Water, USP* | q.s. | — |
| Total | 100.00 | 100.00 mg |

*removed by drying

EXAMPLE 4

Employing the above procedures a 10 milligram strength entecavir capsule was prepared.

| Ingredient | Amount % weight/weight | Amount per capsule |
|---|---|---|
| Entecavir | 10.00 | 10.00 mg |
| Microcrystalline cellulose, NF | 82.03 | 82.03 mg |
| Crospovidone, NF | 4.00 | 4.00 mg |
| Povidone, USP | 2.50 | 2.50 mg |
| Magnesium Stearate, NF | 0.25 | 0.25 mg |
| Hydrochloric acid | 1.22 | 1.22 mg |
| Purified Water, USP* | q.s. | — |
| Total | 100.00 | 100.00 mg |
| Capsule shell | — | |

*removed by drying

EXAMPLE 5

Employing the above procedures a 0.05 milligram strength entecavir capsule was prepared.

| Ingredient | Amount % weight/weight | Amount per capsule |
|---|---|---|
| Entecavir | 0.05 | 0.05 mg |
| Dicalcium phosphate, NF | 93.20 | 93.20 mg |
| Crospovidone, NF | 4.00 | 4.00 mg |
| Hydroxypropyl cellulose, NF | 2.50 | 2.50 mg |
| Magnesium Stearate, NF | 0.25 | 0.25 mg |
| Purified Water, USP* | q.s. | — |
| Total | 100.00 | 100.00 mg |
| Capsule shell | — | |

*removed by drying

EXAMPLE 6

Employing the above procedures a tablet of 1 milligram strength entecavir was prepared.

| Ingredient | Amount % weight/weight | Amount per tablet |
|---|---|---|
| Entecavir | 1.00 | 1.00 mg |
| Mannitol, NF | 90.00 | 90.00 mg |
| Croscarmellose sodium, NF | 4.00 | 4.00 mg |
| Methyl Cellulose, NF | 2.50 | 2.50 mg |
| Stearic Acid, NF | 2.50 | 0.25 mg |
| Purified Water, USP* | q.s. | — |
| Total | 100.00 | 100.00 mg |

*removed by drying

EXAMPLE 7

Employing the above procedures a tablet of 0.5 milligram strength entecavir was prepared.

| Ingredient | Amount % weight/weight | Amount Per Tablet, mg |
|---|---|---|
| Entecavir | 0.25 | 0.5 |
| Lactose Monohydrate, NF | 60.25 | 120.5 |
| Microcrystalline Cellulose, NF | 32.50 | 65.0 |
| Crospovidone, NF XL-10 | 4.0 | 8.0 |
| Povidone, NF K-30 | 2.50 | 5.0 |
| Magnesium Stearate, NF | 0.50 | 1.0 |
| Purified Water | q.s. | — |
| Total | 100.0% | 200.0 mg |

The entecavir was dissolved in upto 17% w/w aqueous povidone solution which was heated at 60 to 70° C.

EXAMPLE 8

The 100 mg tablet of Example 1 containing 0.5 mg of entecavir, the 100 mg tablet of Example 2 containing 0.1 mg of entecavir, the 100 mg tablet of Example 3 containing 0.01 mg of entecavir, the 100 mg tablet of Example 6 containing 1.0 mg of entecavir, and the 200 mg tablet of Example 7 containing 0.5 mg of entecavir can be film coated with the composition set forth below using conventional pan coating or spray coating techniques.

| Ingredient | Amount % weight/weight | Amount per tablet[1] |
|---|---|---|
| Opadry ® | 1 to 10 | 1 to 10 mg |
| Plasticizer[2] | 0 to 10 | 0 to 10 mg |
| Purified Water, USP* | q.s. | — |

*removed by drying
Opadry ® is commercially available and contains hydroxypropylmethylcellulose, titanium dioxide, polyethylene glycol, polysorbate 80, synthetic yellow iron oxide and synthetic red iron oxide.
[1]The calculations are done assuming a tablet weight of 100 mg.
[2]Suitable plasticizers are diethyl citrate and triethyl citrate.

EXAMPLE 9

The safety and antiviral activity of entecavir given for 28 days to human subjects with chronic hepatitis B virus infection was studied in a randomized, double-blind, placebo-controlled, dose-escalating trial. Entecavir demonstrated potent antiviral activity at all doses tested. The mean log reduction in hepatitis B virus DNA viral levels in the blood at day 28 were 2.21, 2.25, 2.81, and 2.42 for the 0.05, 0.1, 0.5 and 1.0 mg once daily doses of entecavir, respectively. Entecavir was well tolerated.

EXAMPLE 10

The safety and antiviral activity of three doses of entecavir (0.01 mg, 0.1 mg and 0.5 mg) given once daily for 24 weeks were studies in adults with chronic hepatitis B in a randomized, double-blind, lamivudine (100 mg QD) controlled trial. All three doses of entecavir demonstrated potent antiviral activity. The two higher doses of entecavir produced significantly greater reductions in hepatitis B virus DNA viral levels in blood compared to lamivudine. Entecavir at all doses was well tolerated.

What is claimed is:

1. A pharmaceutical composition effective for once a day oral administration to treat hepatitis B virus infection in a human adult patient comprising a pharmaceutically acceptable carrier and from about 0.01 mg to about 5 mg of entecavir.

2. The composition of claim 1 wherein said entecavir is present at about 0.01 mg.

3. The composition of claim 1 wherein said entecavir is present at about 0.05 mg.

4. The composition of claim 1 wherein said entecavir is present at about 0.1 mg.

5. The composition of claim 1 wherein said entecavir is present at about 0.5 mg.

6. The composition of claim 1 wherein said entecavir is present at about 1.0 mg.

7. The composition of claim 1 wherein the form of a tablet or capsule.

8. The composition of claim 1 containing one or more other pharmaceutically active substances.

9. A phrarmaceutical composition for oral administration of a low dose of entecavir comprising:
   from about 0.001 mg to about 10 mg of entecavir adhered to a carrier substrate wherein said carrier substrate is selected from lactose, microcrystalline cellulose, calcium phosphate, dextrin, dextrose, dextrates, mannitol, sorbitol and sucrose, and mixture thereof, and
   said entecavir is adhered to said substrate by an adhesive substance which is a polymeric material possessing sufficient tack.

10. The composition of claim 9 wherein:
    said adhesive substance is selected from povidone, methylcellulose, hydroxymethylcellulose, hydroxypropyl-methylcellulose, hydroxypropylcellulose, hydroxyethylcellulose, gelatin, guar gum, and xanthan gum and mixtures thereof.

11. The composition of claim 9 including a lubricant and a disintegrant.

12. The composition of claim 11 wherein:
    said lubricant is selected from magnesium stearate, stearic acid, sodium stearyl fumarate, and sodium lauryl sulfate, and mixtures thereof and said disintegrant is selected from crospovidone, croscarmellose sodium, sodium starch glycolate, pregelatinized starch, and corn starch and mixtures thereof.

13. A pharmaceutical composition effective for once a day oral administration to treat hepatitis B virus infection in a human patient comprising a pharmaceutically acceptable carrier and about 0.01 mg of entecavir.

14. The composition of claim 13 in the form of a tablet or capsule.

15. The composition of claim 13 containing one or more other pharmaceutically active substances.

16. A pharmaceutical composition for oral administration of a low dose of entecavir comprising entecavir coated by means of an adhesive substance to a carrier substrate, a lubricant, and a disintegrant wherein:
   said entecavir is present at from about 0.001 to about 10% by weight of said composition,
   said adhesive substance is present at from about 0.01 to about 10% by weight of said composition,
   said carrier substrate is present at from about 80 to about 95% by weight of said composition,
   said disintegrant is present at from about 1 to about 7% by weight of said composition, and
   said lubricant is present at from about 0.1 to about 5% by weight of said composition.

17. A composition of claim 16 wherein:
   said adhesive substance is selected from povidone, methylcellulose, hydroxymethylcellulose, hydroxypropyl-methylcellulose, hydroxypropylcellulose, hydroxyethyl-cellulose, gelatin, guar gum, and xanthan gum and mixtures thereof,
   said carrier substrate is selected from lactose, microcrystalline cellulose, calcium phosphate, dextrin, dextrose, dextrates, mannitol, sorbitol, and sucrose and mixtures thereof,
   said disintegrant is selected from crospovidone, croscarmellose sodium, sodium starch glycolate, pregelatinized starch, and corn starch, and mixtures thereof, and
   said lubricant is selected from magnesium stearate, stearic acid, sodium stearyl fumarate, and sodium lauryl sulfate, and mixtures thereof.

18. A composition of claim 17 wherein:
   said adhesive substance is povidone.

19. A composition of claim 17 wherein:
   said carrier substrate is microcrystalline cellulose or lactose or mixtures thereof.

20. A composition of claim 17 wherein:
   said disintegrant is crospovidone.

21. A composition of claim 17 wherein:
   said lubricant is magnesium stearate.

22. The low dose entecavir tablet composition comprising:
   about 0.01% entecavir,
   about 93.24% microcrystalline cellulose,
   about 4.0% crospovidone,
   about 2.50% povidone, and
   about 0.25% magnesium stearate, said percentages being on a weight/weight basis.

23. The low dose entecavir tablet composition comprising:
   about 1.0% entecavir,
   about 90.0% mannitol,
   about 4.0% croscarmellose sodium,
   about 2.50% methyl cellulose, and
   about 2.50% stearic acid, said percentages being on a weight/weight basis.

24. The low dose entecavir tablet composition comprising:
   about 0.5% entecavir,
   about 60.00% lactose monohydrate,
   about 32.50% microcrystalline cellulose,
   about 4.0% crospovidone,
   about 2.50% povidone, and
   about 0.50% magnesium stearate, said percentages being on a weight/weight basis.

25. The low dose entecavir tablet composition comprising:
   about 0.1% entecavir,
   about 60.00% lactose monohydrate,
   about 35.39% microcrystalline cellulose,
   about 4.0% crospovidone,
   about 0.01% povidone, and
   about 0.5% magnesium stearate, said percentage being on a weight/weight basis.

26. The low dose entecavir tablet composition comprising:
   about 0.25% entecavir,
   about 60.25% lactose monohydrate,
   about 32.50% microcrystalline cellulose,
   about 4.0% crospovidone,
   about 2.50% povidone, and
   about 0.5% magnesium stearate, said percentages being on a weight/weight basis.

27. The low dose entecavir tablet composition of claim 22 having an outer film coating.

28. The low dose entecavir tablet composition of claim 23 having an outer film coating.

29. The low dose entecavir tablet composition of claim 24 having an outer film coating.

30. The low dose entecavir tablet composition of claim 25 having an outer film coating.

31. The low dose entecavir tablet composition of claim 26 having an outer film coating.

32. The low dose entecavir capsule composition comprising:
   about 10.0% entecavir,
   about 82.03% microcrystalline cellulose,
   about 4.00% crospovidone,
   about 2.50% povidone,
   about 0.25% magnesium stearate, and about 1.22% hydrochloric acid, said percentages being on a weight/weight basis.

33. The low dose entecavir capsule composition comprising:
   about 0.05% entecavir,
   about 93.20% dicalcium phosphate,
   about 4.00% crospovidone,
   about 2.50% hydroxypropyl cellulose, and
   about 0.25% magnesium stearate, said percentages being on a weight/weight basis.

34. A pharmaceutical composition effective for once a day oral administration to treat hepatitis B virus infection in a human patient comprising a pharmaceutically acceptable carrier and about 0.05 mg of entecavir.

35. The composition of claim 34 in the form of a tablet or capsule.

36. The composition of claim 34 containing one or more other pharmaceutically active substances.

37. A pharmaceutical composition effective for once a day oral administration to treat hepatitis B virus in a human patient comprising a pharmaceutically acceptable carrier and about 0.1 mg of entecavir.

38. The composition of claim 37 in the form of a tablet or capsule.

39. The method of treating a patient infected with hepatitis B virus infection or co-infected with hepatitis B and another viral or non-viral disease comprising administering a pharmaceutical composition containing from about 0.001 mg to about 25 mg of entecavir on a daily basis.

40. The method of claim 39 wherein:

said pharmaceutical composition administered on a daily basis contains from about 0.01 mg to about 10 mg of entecavir.

41. The method of claim 39 wherein said pharmaceutical composition administered on a daily basis contains from about 0.01 mg to about 5 mg of entecavir.

42. The method of claim 39 wherein said entecavir composition is administered along with a second composition containing one or more antiviral agents and/or one or more immunomodulators.

43. The method of claim 42 wherein said entecavir composition and said second composition are combined into a single dosage form for co-administration.

44. The method of claim 42 wherein said entecavir composition and said second composition are separate dosage forms for a co-administration or sequential administration according to a prescribed schedule.

45. The method of treating a patient infected with hepatitis B virus infection comprising orally administering a pharmaceutical composition containing from about 0.001 mg to about 25 mg of entecavir on a daily basis until the infection is no longer active and then orally administering a pharmaceutical composition containing from about 0.01 mg to about 25 mg of entecavir on a less than daily regimen.

46. A method of preparing a pharmaceutical composition of entecavir for oral administration containing from about 0.001 to about 10% on a weight/weight basis of entecavir comprising:

(a) dissolving said entecavir and an adhesive substance in a solvent wherein said solvent is water or water having an acidic or basic pH, (b) spraying said solution form step (a) onto a carrier substrate while said carrier substrate is in motion, (c) drying said coated carrier substrate from step (b) to remove said solvent, and (d) combining said dried coated carrier substrate from step (c) with other desired ingredients to form said pharmaceutical composition.

47. The method of claim 46 wherein:

said carrier substrate is kept in motion during spraying step (b) by mechanical agitation, and said coated carrier substrate is dried in step (c) in a tray drier or fluidbed drier.

48. The method of claim 46 wherein:

said carrier substrate is kept in motion during spraying step b) by air stream, and said coated carrier substrate is dried in step (c) also by means of air stream agitation.

49. The method of claim 46 wherein said adhesive substance in step (a) is selected from the group consisting of povidone, methylcellulose, hydroxymethylcellulose, hydroxypropylmethylcellulose, hydroxypropylcellulose, hydroxyethylcellulose, gelatin, guar gum, xanthan gum and mixtures thereof.

50. The composition of claim 37 containing one or more other pharmaceutically active substances.

51. A pharmaceutical composition effective for once a day oral administration to treat hepatitis B virus infection in a human patient comprising a pharmaceutically acceptable carrier and about 0.5 m of entecavir.

52. The composition of claim 51 in the form of a tablet or capsule.

53. The composition of claim 51 containing one or more other pharmaceutically active substances.

\* \* \* \* \*

UNITED STATES PATENT AND TRADEMARK OFFICE
CERTIFICATE OF CORRECTION

PATENT NO.    : 6,627,224 B2
DATED         : September 30, 2003
INVENTOR(S)   : Colonno et al.

It is certified that error appears in the above-identified patent and that said Letters Patent is hereby corrected as shown below:

Column 12,
Line 34, "and about 0.5 m of entecavir." should read -- and about 0.5 mg of entecavir. --

Signed and Sealed this

Fourth Day of January, 2005

JON W. DUDAS
*Director of the United States Patent and Trademark Office*